United States Patent [19]

Walt

[11] Patent Number: 5,254,477
[45] Date of Patent: * Oct. 19, 1993

[54] FLOURESCENCE INTRAMOLECULAR ENERGY TRANSFER CONJUGATE COMPOSITIONS AND DETECTION METHODS

[75] Inventor: David R. Walt, Lexington, Mass.

[73] Assignee: Trustees of Tufts College, Medford, Mass.

[*] Notice: The portion of the term of this patent subsequent to Sep. 1, 2009 has been disclaimed.

[21] Appl. No.: 762,245

[22] Filed: Sep. 19, 1991

Related U.S. Application Data

[63] Continuation of Ser. No. 294,175, Jan. 6, 1989, abandoned, which is a continuation-in-part of Ser. No. 878,128, Jun. 25, 1986, Pat. No. 4,822,746.

[51] Int. Cl.$^5$ .................. G01N 21/64; G01N 21/80; C12Q 1/00
[52] U.S. Cl. ..................... 436/172; 436/71; 436/95; 436/164; 436/536; 436/537; 436/501; 435/4; 435/11; 435/14; 435/15
[58] Field of Search ............... 436/536, 537, 501, 56, 436/164, 165, 172, 518, 528, 546, 800, 805, 95, 71; 435/4, 11, 14, 15

[56] References Cited

U.S. PATENT DOCUMENTS 5,143,853 9/1992 Walt .................... 436/501

Primary Examiner—Toni R. Scheiner
Attorney, Agent, or Firm—David Prashker

[57] ABSTRACT

A variety of conjugated compositions and methods for the detection of an analyte of interest in a fluid sample is provided which relies upon an intramolecular energy transfer between a conjugated fluorophore and a chromophoric light-absorbing ligand for qualitative and quantitative results. The detection methods preferably employ fiber optic sensors in combination with analyte-insensitive fluorophores and analyte-sensitive absorber ligands in conjugated form. The methods and compositions rely upon the ability of the absorbing ligands to absorb energy which is transferred non-radiatively by the fluorophore when in an excited state.

4 Claims, 5 Drawing Sheets

PHENOL RED

ALLYL-5-THIOUREA EOSIN

ACCEPTOR

DONOR

PHENOL RED
▲ pH 4.0
● pH 8.0

EOSIN
■ ABSORPTION
--- EMISSION

FLOURESCENCE INTRAMOLECULAR ENERGY TRANSFER CONJUGATE COMPOSITIONS AND DETECTION METHODS

CROSS-REFERENCE

This application is a continuation of application Ser. No. 294,175 filed Jan. 6, 1989, now abandoned, which is a continuation-in-part of patent application Ser. No. 878,128 filed Jun. 25, 1986, now U.S. Pat. No. 4,822,746.

FIELD OF THE INVENTION

The present invention is generally concerned with fluorescence detection methods and apparatus and is directed to methods and compositions which qualitatively and/or quantitatively can detect an analyte of interest using absorbance modulated fluorescence.

BACKGROUND OF THE INVENTION

Fluorescence is a physical phenomenon based upon the ability of some molecules to absorb and emit light. With some molecules, the absorption of light (photons) at specified wavelengths is followed by the emission of light from the molecule of a longer wavelength and at a lower energy state. Such emissions are called fluorescence and the emission lifetime is said to be the average period of time the molecule remains in an excited energy state before it emits light of the longer wavelength. Substances which release significant amounts of fluorescent light are termed "fluorophores" and are divisible into two broad classes: intrinsic fluorescent substances and extrinsic fluorescent substances. Intrinsic fluorophores comprise the naturally occuring biological molecules whose demonstrated ability to absorb exciting light and emit light of longer wavelengths is directly based on their internal structure and chemical formulation. Typical examples include proteins and polypeptides containing tryptophan, tyrosine, and phenylalanine. In addition, enzymatic cofactors such as NADH, FMN, FAD, and riboflavin are highly fluorescent. Extrinsic fluorophores, for the most part, do not occur in nature and have been developed for use as dyes to label proteins, immunoglobulins, lipids, and nucleic acids. This broad class includes fluorescein, rhodamine, and their isocyanates and isothiocyanate derivatives; dansyl chloride; naphthylamine sulfonic acids such as 1-anilino-8-naphthalene sulfonic acid ("ANS") and 2-p-toluidinylnaphthalene-6-sulfonic acid ("TNS") and their derivatives; acridine orange; proflavin; ethidium bromide; quinacrine chloride; and the like.

Substances able to fluoresce share and display a number of common characteristics: fluorophores display the ability to absorb light at one wavelength or frequency, reach an excited energy state, and subsequently emit light at another light frequency and energy level. The excitation spectrum and fluorescence emission spectrum are individual for each fluorophore and are often graphically represented as two separate curves which are slightly overlapping. The absorption and emission spectra for quinine bisulfate is depicted in FIG. 1 and is representative of fluorescent substances in general. All fluorophores demonstrate the Stokes' Shift—that is, the emitted light is always at a longer wavelength (and at a lower energy level) relative to the wavelength (and the energy level) of the exciting light absorbed by the substance. Moreover, the same fluorescence emission spectrum is generally observed irrespective of the wavelength of the exciting light; accordingly, the wavelength and energy of the exciting light may be varied within limits, but the light emitted by the fluorophore will provide the same emission spectrum. Finally, fluorescence may be measured as the quantum yield of light emitted; the fluorescence quantum yield is the ratio of the number of photons emitted in comparison to the number of photons absorbed. The quantum yield of photons and the timed duration over which that quantity of emitted light is detectable may be modified by a variety of factors. For more detailed information regarding each of these characteristics the following references are recommended: Lakowicz, J. R., *Principles Of Fluorescence Spectroscopy*, Plenum Press, New York, 1983; Freifelder, D., *Physical Biochemistry*, Second Edition, W. H. Freeman and Company, New York, 1982.

Analytical methods utilizing extrinsic fluorophores have had to conform to several specific requirements in order to be useful: (1) The extrinsic fluorophore must be capable of being tightly bound at a specific location or reactive to a unique chemical entity. (2) Its fluorescence must be sensitive to those changes in the environmental test conditions or system indicative of a chemical change. (3) The extrinsic fluorophore should not directly affect the features or properties of the molecule being investigated. Alternatively, however, the user has the option to use extrinsic fluorophores that react with an analyte in either a reversible or irreversible manner. If used irreversibly, fresh fluorophore must be added to the test sample each time an analysis is performed. In practical effect, this has required the investigator to adapt one of two functional approaches: to utilize fluorophores which themselves demonstrate the capacity to specifically bind to a preselected ligand or analyte of interest; or to alteratively chemically combine a non-specific fluorophore with another composition which has the requisite specific binding capacity to form a conjugate molecule, the binding specificity of the conjugate being provided by the other compound while the light emitting capability is provided by the fluorophore. Each approach is exemplified by the presently known qualitative and quantitative assay methods now well established in the art.

For example, the fusion of an extrinsic fluorophore with a specific antibody has been employed in two applications. First, by the use of such fluorescent labelled specific antibody for the study of specific macromolecules or cells in tissue sections. Specific cells or tissues are combined with a conjugate comprising the fluorophore and the antibody which is then applied over a section of prepared tissue; the attachment of the fluorescent labelled antibody identifies the existence of a specific macromolecule within the tissue sections [Coons, A. H., *Int. Rev. Cytol.* 5:1 (1956); Coons, A. H., "Fluorescent Antibody Methods," in *General Cytochemical Methods* (Danielli, J. F., Editor) Academic Press, New York, 1958, pp 399–422; Saint-Marie, G., *J. Histochem.* 10:250 (1962)].

A second example is the use of extrinsic fluorophores in immunoassays:: The fluorescent substance is again utilized as an identifying label with an immunogen whose presence in homogeneous and/or heterogeneous assays identifies the presence of a specific partner. Typically these include antibody-antigen reactions in competitive and non-competitive protocols [White, R. G., "Fluorescent Antibody Techniques," in *Immunological Methods*, (Ackroyd, J. F., Editor), Blackwell, Oxford, 1964; Nairn, R. C., *Fluorescent Protein Tracing*, Livingstone, Edinborough; Goldstein, *J. Exp. Med.* 114:89 (1961); Humphrey and White, *Immunology For Students Of Medicine*, Blackwell Scientific Publications, Oxford, England, 1966, pp 226-228].

Examples of using the fluorophore alone include the determination of the heme-binding site in hemoglobin. Hemoglobin is a complex of a small prosthetic group with the protein, apohemoglobin. The extrinsic fluor 1-anilino-8-naphthalene sulfonate (hereinafter "ANS") fluoresces when added to solutions of apohemoglobin but does not fluoresce with hemoglobin alone. The addition of heme to the apohemoglobin-ANS complex eliminates fluorescence by displacement of the ANS; accordingly, the site of attachment for the ANS and for heme must be the same. The timing as well as the location of such binding sites is identified by the fluorescence or elimination of fluorescence provided by ANS.

Similarly, the detection of a conformational change in an enzyme when the substrate becomes bound is detectable by the use of a fluorophore. 2-p-toluidylnaphthalene-6-sulfonate (hereinafter "TNS") fluoresces only if bound to another molecule; TNS fluoresces when added to the enzyme, alphachymotrypsin. The addition of a specific substrate for this enzyme decreases the fluorescence. Accordingly, fluorescence may be used as the means to determine both the degree of binding and the specific catalytic site for the enzyme with respect to the affinity and the location of the enzymatic reactions.

Fluorescence microscopy is another technique which has been utilized with fluorophores which have specific binding capacity and which can be transported and localized intracellularly. For example, acridine orange binds specifically to nucleic acids and fluoresces green or orange if bound to either DNA or RNA respectively. This technique has been used with eukaryotes to observe nucleic acids and chromosomes and to detect RNA in the nucleus; it has also been used with prokaryotes to localize and identify DNA.

By its nature and applications, fluorescence and fluorescent detection methods are recognized as being completely different and distinguishable from light energy absorbance and absorption spectroscopy. When light energy waves encounter a molecule, the light energy can either be scattered or absorbed. If the light energy is absorbed, the molecule is said to be in an excited state and is often termed a "chromophore" or an "absorber." Molecules which absorb light and do not fluoresce usually convert the light energy into heat or kinetic energy unlike fluorescent molecules which re-emit the light at lower energy levels. The ability to internally convert the absorbed light energy rather than emit it as light of another wavelength is a primary difference between absorbers and fluorophores.

Molecules which absorb light energy do so at individual wavelengths and are characterized by a distinctive molar absorption (extinction) coefficient at that wavelength. Chemical analyses utilizing absorption spectroscopy using visible and ultraviolet light wavelengths in combination with the absorption (extinction) coefficient allow for the determination of concentration for specific compositions, for the assay of chemical reactions, and for the identification of individual compounds by spectral measurement. The most common use of absorbance measurement is to determine concentration which is calculated in accordance with Beer's law; accordingly, at a single absorbance wavelength, the greater the quantity of the composition which absorbs light at the single wavelength, the greater the optical density for the sample. In this way, the total quantity of light absorbed is directly correlated with the quantity of the composition in the sample.

Another application lies in those chemical reactions in which one of the reactants changes its absorbance characteristics during the course of the reaction; a common example from enzymology is the use of an enzyme to convert a substrate into a product or products, in which the substrate and/or product absorbs light at a given wavelength. Accordingly, the more of the reaction product that is formed, the greater the change in the quantity of light absorbed. The optical density change over time thus provides a quantitative measure of the activity for that enzyme.

In addition to these, some very sophisticated model systems employing fluorescence have been developed. These include: quenching of fluorescence; and energy transfer system utilizing fluorescent light energy. Basic principles of both these systems are well described within Joseph R. Lakowicz, *Principles of Fluorescence Spectroscopy*, Plenum Press, New York and London, 1984, pages 257-339.

Fluorescence quenching refers to any process which decreases the fluorescence intensity of a given substance and can occur via a variety of different mechanisms such as excited state reactions, energy transfer, complex formation, and collisional quenching. Quenching can be dynamic (or collisional) in nature which results from collisional encounters between a fluorophore and a quencher molecule; alternatively, quenching can be static in nature and result from the formation of complexes between the fluorophore and the quencher. In comparison, fluorescence energy transfer is a mechanism of action in which a transfer of the excited state energy is made from a donor molecule to an acceptor entity. This kind of transfer occurs without the appearance of a photon from the donor and is thus non-radiative in nature; and is deemed to be primarily the result of dipole-dipole interactions between the donor and acceptor compositions. The rate of non-radiative energy transfer depends upon the extent of overlap of the emission spectrum of the donor with the absorption spectrum of the acceptor, the relative orientation of the donor and acceptor dipoles, and the spatial distance between the donor and acceptor molecules. It is this latter limitation and dependence upon spatial distance between the acceptor and donor molecules which has led to the now common use of energy transfer as a means for measuring distances between a donor and acceptor in solution. Detailed investigations of fluorescence quenching techniques based on energy transfer mechanisms of action have been reported [Anufrieva, E. V. and Y. Y. Gotlib, *Adv. Polym. Sci.* 40:1 (1981); Slomkowski, S. and M. A. Winnik, *Macromolecules* 19:500 (1986)].

In the traditional and established viewpoint of practitioners in this art, each of the conventionally known fluorescence phenomenon and fluorescent mechanisms of action have been deemed to be individually distinct and separate from one another. The underlying principles established for each physical phenomenon are unique and distinguishable from even closely related light energy systems. Insofar as is presently known, therefore, there has been no method or technique which has physically joined a fluorophore and an absorber together as a conjugate composition and then employed the conjugate composition in an energy transfer mechanism of action for the quantitative and/or qualitative detection of an analyte.

SUMMARY OF THE INVENTION

The present invention provides a conjugate composition useful for detecting an analyte of interest in a fluid sample, said conjugate composition comprising:

at least one analyte-insensitive fluorophore able to:
(a) absorb exciting light energy of a first wavelength,
(b) non-radiatively transfer at least a portion of said exciting energy to an absorber, and
(c) emit another portion of said exciting energy as emitted light of a second wavelength;

at least one analyte sensitive absorber able to absorb energy transferred non-radiatively by said fluorophore, said absorber being held at a spatial distance of not more than 100 Angstroms from said fluorophore; and means for holding said absorber at said spatial distance from said fluorophore such that a conjugate composition is formed.

The present invention also provides a method for detecting an analyte of interest in a fluid sample, said method comprising the steps of:

obtaining a conjugate composition comprising:
(a) at least one analyte-insensitive fluorophore able to absorb exciting light energy of a first wavelength, and to non-radiatively transfer at least a portion of said exciting energy to an absorber, and to emit another portion of said exciting energy as emitted light of a second wavelength,
(b) at least one analyte-sensitive absorber able to absorb energy transferred non-radiatively by said fluorophore, said absorber being held at a spatial distance of not more than 100 Angstroms from said fluorophore, and
(c) means for holding said absorber at said spatial distance from said fluorophore such that a conjugate composition is formed;

admixing said fluid containing said analyte of interest with said conjugate composition;

introducing exciting light energy of the first wavelength to said admixture sufficient to cause said conjugated fluorophore to emit light of the second wavelength, at least a portion of said exciting energy being non-radiatively transferred to and absorbed by said conjugated absorber; and detecting said light of the second wavelength emitted from said admixture after absorption of energy by said conjugated composition, said detected emitted light being a measure of the analyte of interest in the sample.

DETAILED DESCRIPTION OF THE DRAWING

The present invention may be more easily and completely understood when taken in conjunction with the accompanying drawing, in which.

DETAILED DESCRIPTION OF THE PREFERRED EMBODIMENTS

Figure 1:
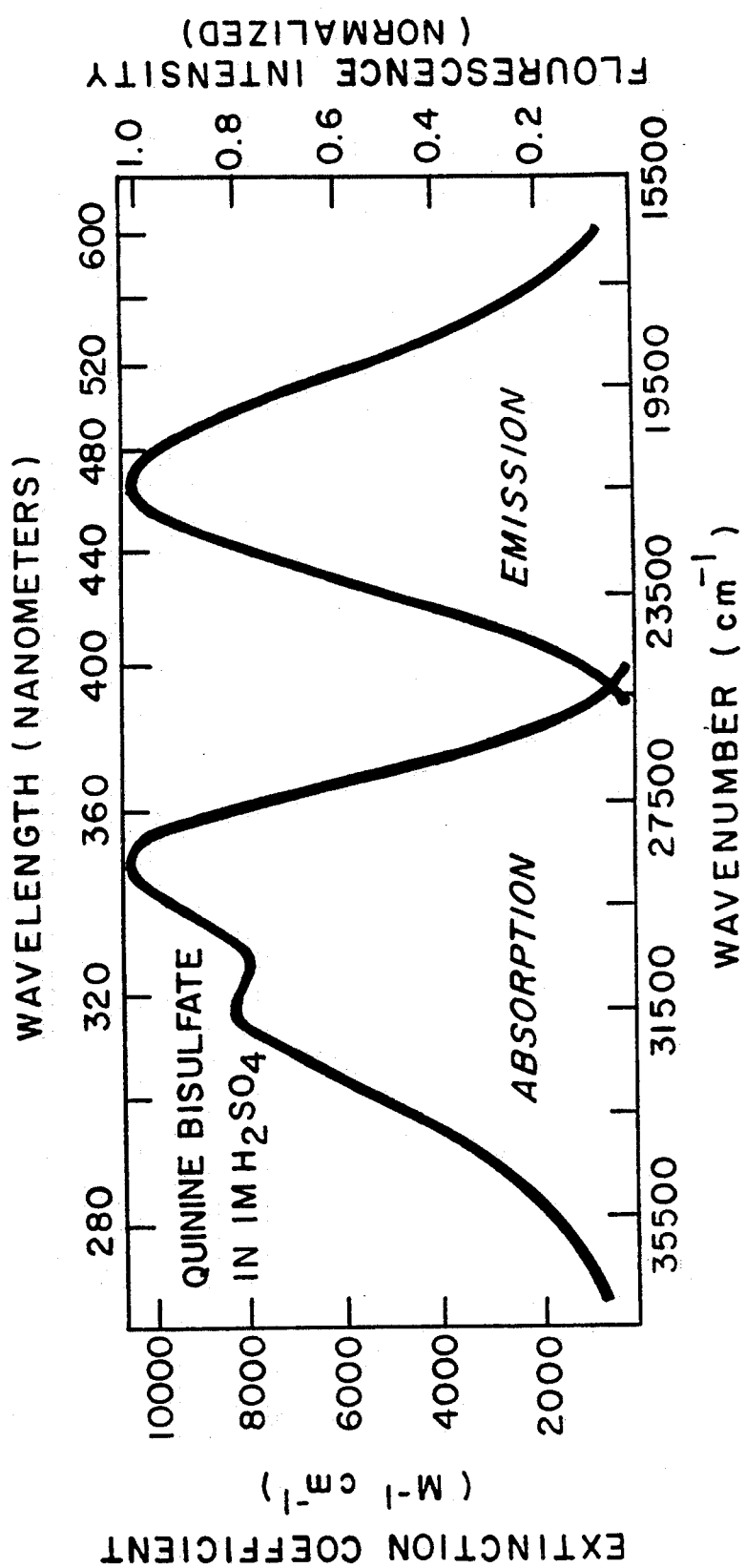
FIG. 1 is a graphic illustration of the absorption and fluorescent emission spectra of quinine bisulfate.

The present invention is a novel methodology performable in various modes for the qualitative and/or quantitative detection of an analyte of interest in a fluid sample using analyte-insensitive fluorophores, analyte-sensitive absorbers, and conventional instrumentation for measuring fluorescence. The invention is unique in that known fluorogenic substances are combined to form conjugates with known light-absorbing ligands and light-absorption complexes, collectively termed "absorbers"; and in which the absorber components of the conjugate absorb, and thus modulate, at least a portion of the energy transferred non-radiatively by the excited energy state fluorophore of the conjugate in a reaction admixture. In this manner, the principles of absorption spectroscopy in which absorber ligands (and absorption complexes) are able to absorb energy without subsequent light emission are thus combined for analytical purposes with the principles of fluorescence spectroscopy in which fluorophores absorb light at one wavelength with a subsequent emission of fluorescent light at another wavelength. The interrelationship between the energy accepting absorber entity and the light excitable fluorogenic substance comprising the conjugate composition relies upon there being a definable spectral overlap between the emission spectrum of the fluorophore and the absorption spectrum of the absorber; and upon there being a set spatial distance of less than 100 Angstroms between the fluorophore and absorber within the conjugate structure. These requirements serve as the basis for the detection methods and apparatus comprising the present invention.

There are only three elements necessary to practice the detection methods of the present invention. These are: (1) a fluorophore-absorber conjugate composition; (2) means for introducing exciting light energy to the conjugate composition; and (3) means for detecting emitted light released by the conjugate composition.

A Fluorophore-Absorber Conjugate Composition

The analyte-sensitive component of the conjugate can take form as either a light-absorbing ligand or a light-absorption complex having a definable light absorption spectrum. Such compositions are generally termed "absorbers" herein to distinguish them readily in text from fluorophores. Absorbers, regardless of their chemical formulation or structure, are recognized and characterized by their ability to absorb light at a specific wavelength with internal conversion of light energy into heat or kinetic energy; their representation by an individual, absorption coefficient which may be determined empirically in the conventional manner; and their ability to absorb light energy in accordance with Beer's law such that absorbance measurements (spectrophotometry) may be used to determine concentration. Within the conjugate structure, it is only the absorber molecule which is sensitive to and affected by the presence of the analyte of interest in a test sample.

The other component of the conjugate composition is an analyte-insensitive fluorophore or fluorogenic substance having a definable light absorbance spectrum and a definable light emission spectrum. Such fluorophores, prior to their conjugation, are able to absorb exciting light (energy) of a first wavelength and subsequently to emit light (energy) of a second wavelength, commonly recognized as fluorescent light. The fluorophore employed in the conjugate must demonstrate two critical characteristics: the emission spectrum of the fluorophore must overlap to some measurable degree with the light absorption of the absorber (prior to conjugation); and the fluorophore is positioned and held at a preset or fixed spatial distance which is less than 100 Angstroms from an absorber within the conjugate composition structure. The manner in which the fluorophore becomes fixed at a set distance from the absorber may vary substantially.

It will be recognized and appreciated that while two different mechanisms of energy transfer between fluorophores and absorbers are known, only one occurs in the conjugate composition. The first known mechanism occurs when a fluorescent substance absorbs light at a first wavelength, reemits light at a second different wavelength (fluoresces), and the emitted light of the second wavelength is absorbed by another different molecular species. The absorbance of light energy in this manner is known as "radiative transfer." The second known mechanism of action involves transfer of excitation energy per se which is no longer in the form of light. It occurs when a fluorophore absorbs exciting light of a first wavelength and is converted into an excited state. During the lifetime of this excited state, the excited fluorescent substance can transfer energy as such to an absorber species without use of radiating light. This type of energy transfer is termed "non-radiative energy transfer." In both forms of transfer, the second molecular species, the absorber, must have energy absorption levels that overlap with the excited state energy levels of the fluorophore. The existence and degree of energy level overlap is most easily determined by examining the fluorophore's light emission spectrum to ensure that it overlaps to some extent with the light absorption spectrum of the absorber species. It will be understood, however, that within the conjugate compositions and methods comprising the present invention herein, only the non-radiative energy transfer mechanism is operative.

Mathematical Basis For Constructing The Fluorophore-Absorber Conjugate Composition The theoretical basis and mathematical model to describe fluorescence modulation by absorbing species has been published [Yuan and Walt, *Anal. Chem.* 59:2391 (1987)]. As the results of theoretical studies have demonstrated, in general, solution based systems cannot exhibit significant energy transfer properties. This is a consequence of the large intermolecular distances in solution resulting from the relatively low concentrations of donor and acceptor. The efficiency of singlet dipole-dipole energy transfer is predicted by Forster theory [Forster, T., *Faraday Discuss. Chem. Soc.* 27:7 (1959)]as follows:

$$E = R_o^6 / R_o^6 + R^6 \quad \text{(Equ. 1)}$$

R is the distance between the two chromophores and $R_o$ is the distance at which energy transfer is 50%. $R_o$ depends on the refractive index of the medium between donor and acceptor, n, the spectral overlap of donor fluorescence and acceptor absorption, J, the quantum yield of the donor, $\phi_d$ and a geometric factor, $K^2$.

$$R_o = 9.79 \times 10^3 (J \, n^{-4} \phi_d K^2)^{1/6} \quad \text{(Equ. 2)}$$

The geometric factor, $K^2$, is the angular part of the dipole-dipole interaction tensor averaged over all orientations of donor and acceptor. For freely rotating donor and acceptor, $K^2 = \frac{2}{3}$.

For a solution containing both a donor and an acceptor, each randomly distributed throughout the solution, the relationship between R and the acceptor concentration is:

$$R = (3,000/4\pi N[A])^{\frac{1}{3}} \quad \text{(Equ. 3)}$$

where N is Avogadro's number and [A] is the concentration of acceptor. Therefore, the efficiency of energy transfer is:

$$E = 1/[1 + ([A]_{1/78}/[A])^2] \quad \text{(Equ. 4)}$$

There are thus many systems that will not exhibit significant energy transfer or inner filter effects due to the low extinction coefficients of the absorbing species involved. In order to expand meaningfully the number of species that might be analyzed by fluorescence techniques, the use of non-radiative, intramolecular energy transfer was explored. Intramolecular energy transfer can occur whenever two separated chromophores are incorporated in a single molecule (D~A) with a fixed intramolecular distance (<75 Å). In such cases, control of the spatial relationship between donor and acceptor groups may exist without the randomness characteristics of intermolecular interactions.

There are two known mechanisms for energy transfer in such systems. Forster resonance transfer for long-range dipole-dipole interaction as given by Equ. 1; and Dexter transfer for short-range exchange interaction energy transfer [Dexter, D. L., *J. Chem. Phys.* 21:836 (1953)]. The Dexter mechanism is given by:

$$K_{et} = (2\pi/h) k' J \exp(-2R/L) \quad \text{(Equ. 5)}$$

wherein L is the average orbital radius involved in initial and final states of donor and acceptor; and k' is a constant which, unlike $R_o$, is not related to any experimental parameters. Energy transfer via forbidden transitions are allowed by exchange interactions while they are much less probable in the Forster mechanism. Energy will be transferred mainly by the Forster mechanism unless $R_o < 10$ Å. The critical spatial intramolecular distance thus is a maximum of approximately 100 Angstroms.

Conjugate Structure Implementation

From the theoretical treatment there are two critical parameters that impinge upon the energy transfer efficiency-intramolecular distance and spectral overlap. The fixed distance requirement constrains the fluorescent donor and the absorbing acceptor to be geometrically positioned within a defined range for energy transfer to occur. For Forster transfer (Equ. 1), a distance between 10 and 100 Angstroms is essential. At greater distances, the energy transfer efficiency is essentially zero. Below 10 Angstroms, the Dexter transfer mechanism (Equ. 5) comes into play. The Dexter mechanism also enables efficient energy transfer to occur. When the distance is decreased to 5 Angstroms, the transfer efficiency approaches 100% and further decreases in distance are not observable as changes in fluorescence emission intensity.

Spectral overlap is essential to energy transfer. Without finite overlap, non-radiative energy transfer does not occur. The greater the overlap between the donor's emission and the acceptor's absorption spectrum, the greater the transfer efficiency. Accordingly, the spatial distance and spectral overlap requirements are related. As spectral overlap becomes greater, the distance requirement may be relaxed. Conversely, as the degree of spectral overlap decreases, it is important that the fixed spatial distance be small for efficient non-radiative energy transfer to occur. Thus, the donor acceptor conjugate must provide a spacial relationship between 5 and 100 Angstroms as well as a finite spectral overlap between the fluorophore and absorber species.

Two types of molecular systems can be used for such intramolecular energy transfer. One is a bichromophoric system composed of fluorophore and absorber moieties connected by a flexible —$(CH_2)n$ chain, a flexible derivatized carbon chain, or a rigid cross-linking agent. Means for such construction is conventionally known in the art [S. and J. Katriel, *J. Chem. Phys. Lett.* 102:88 (1983)]. The bichromophores may also possess both rigid and flexible chains concurrently linking the two dyes. In the rigid system, the above fixed distance requirements apply. In flexible systems, however, there is often conformational mobility. In this case, the average intramolecular distance is critical rather than the fully extended spatial distance. For example, a sufficiently long chain linker can connect donor and acceptor such that in the fully extended conformation of the conjugate, the actual spatial distance between donor and acceptor molecules may exceed the 100 Angstrom requirement. However, the flexibility of the linker chain may enable the donor and acceptor to be within effective energy transfer distance a substantial percentage of the time. In this instance then, those conjugates that have donor and acceptor molecules within this average distance during the excited state lifetime will exhibit energy transfer, while those in the fully extended chain conformation will not. Therefore, at any given time some conjugates will be sensitive to analyte while others will not.

In addition, the bichromophore format can be employed reversibly or irreversibly. It will be noted that in some situations the absorber component of the bichromophore may form an irreversible reaction adduct with the analyte of interest in the test sample. In these cases, the bichromophore is irreversible and fresh bichromophore must be added whenever a new measurement of analyte is needed. Alternatively, the reaction of the bichromophore with the analyte is reversible and the bichromophore can be recovered and used again repeatedly.

The other molecular format is a polymer system containing a plurality of energy donors and acceptors positioned at one or more set distances from each other but randomly distributed on the polymer chain. Another special case, however, can occur with polymer systems. In polymers containing multiple donors and acceptors, an event called an "antenna effect" can occur that removes the stringent distance requirements for many donors and acceptors. In these systems, the plurality of donors can act in concert to transfer energy amongst themselves along the polymer length until a donor is excited which is positioned within effective energy transfer distance of an acceptor molecule. In this way, even though the initially excited donor may not be within the requisite energy transfer distance, energy can be transferred among the donors within the polymer until this distance requirement is satisfied. In each of these systems, the intramolecular separation between donor and acceptor can be fixed at a set spatial distance so that fluorescence quenching via energy transfer can be easily detected even at very low concentrations of absorber.

Means For Introducing Exciting Light Energy And Means For Detecting Emitted Light It is intended and expected that known instrumentation will provide both: The means for introducing exciting light (energy) to the fluorophore-absorber conjugate composition sufficient to cause the fluorophore to enter into an excited energy state and to transfer energy non-radiatively to the energy absorbing ligands or absorption complexes of the conjugate; and the means for detecting the emitted light (energy) released by the fluorophore of the conjugate after the total energy excited state has been absorbed in part by the light-absorbing component of the conjugate. The amount of emitted light detected will be the result of the light energy emitted by the fluorophore after prior diminution or modulation of the total excited state energy by the energy-absorbing component in the conjugate composition. In this manner, the actual amount of emitted light detected by the user will vary directly with the concentration of the light-absorbing analyte of interest in the test sample.

Figure 2:
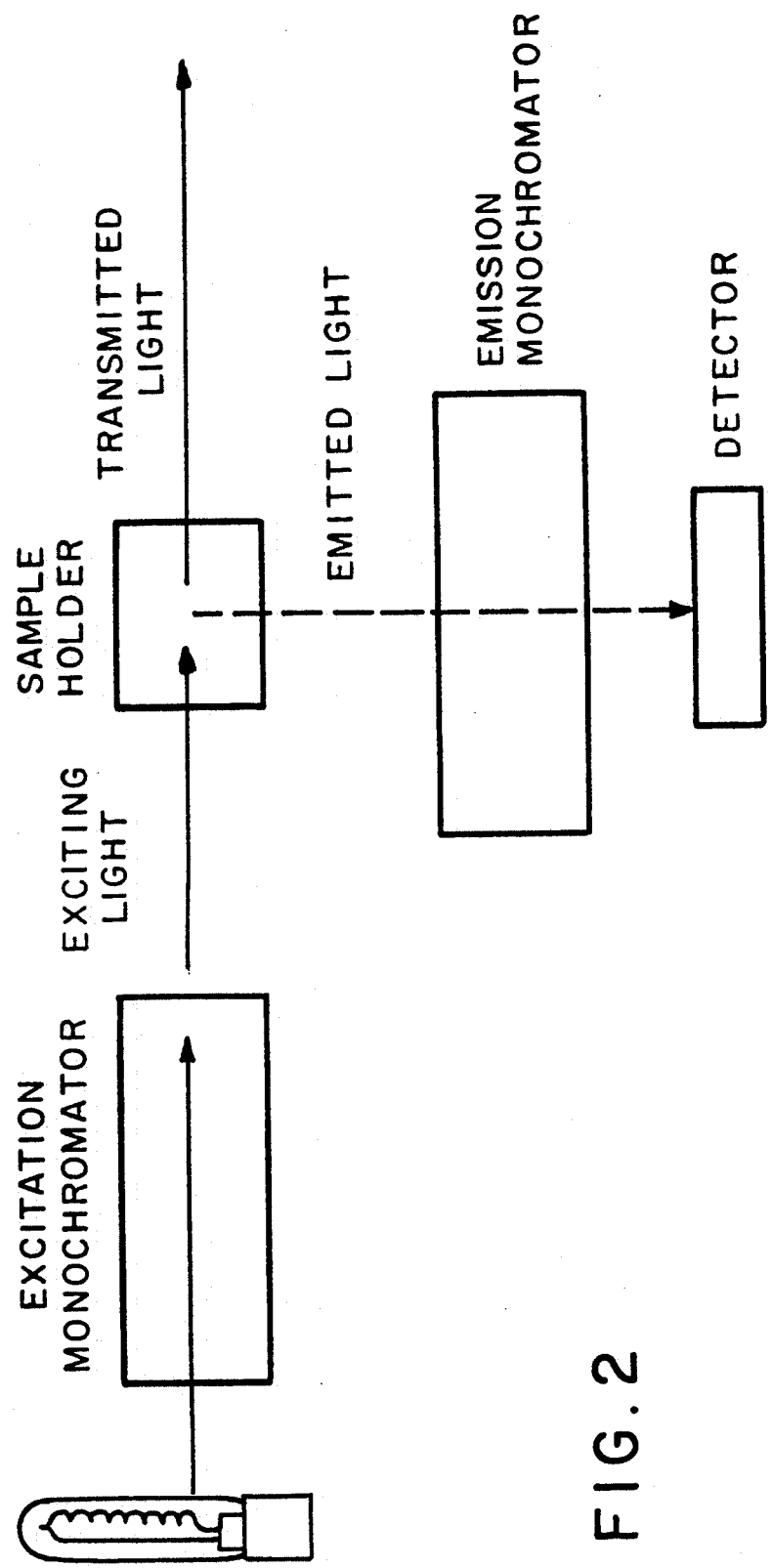
FIG. 2 illustrates the conventional instrumentation for measuring fluorescence.
Figure 3A:
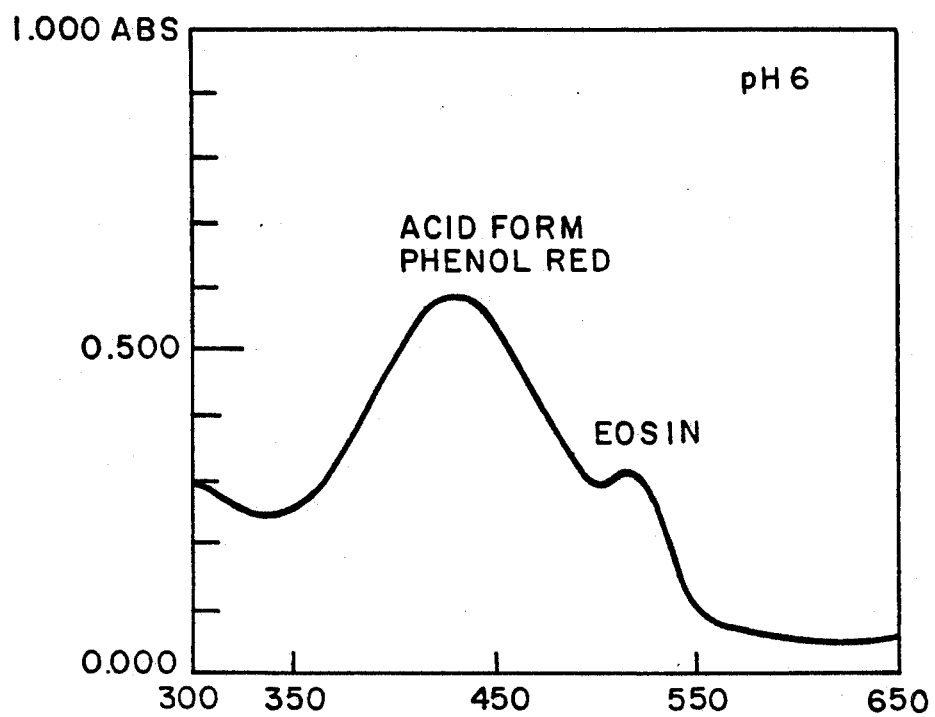
FIGS. 3a, 3b, 3c and 3d are graphs illustrating the detection of emitted light as a function of changes in pH.
Figure 3B:
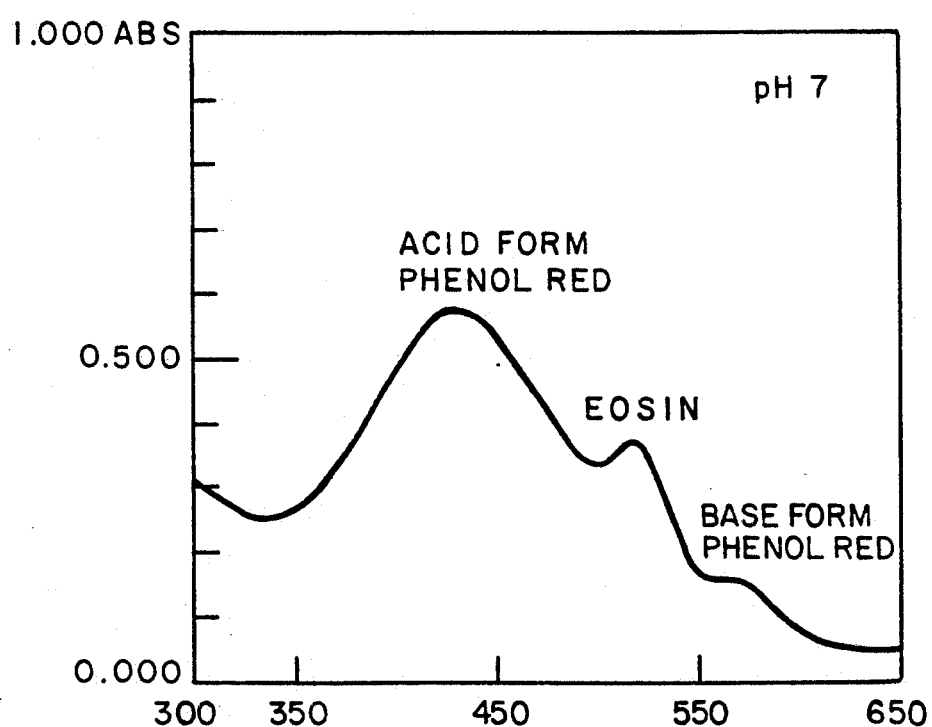
Figure 3C:
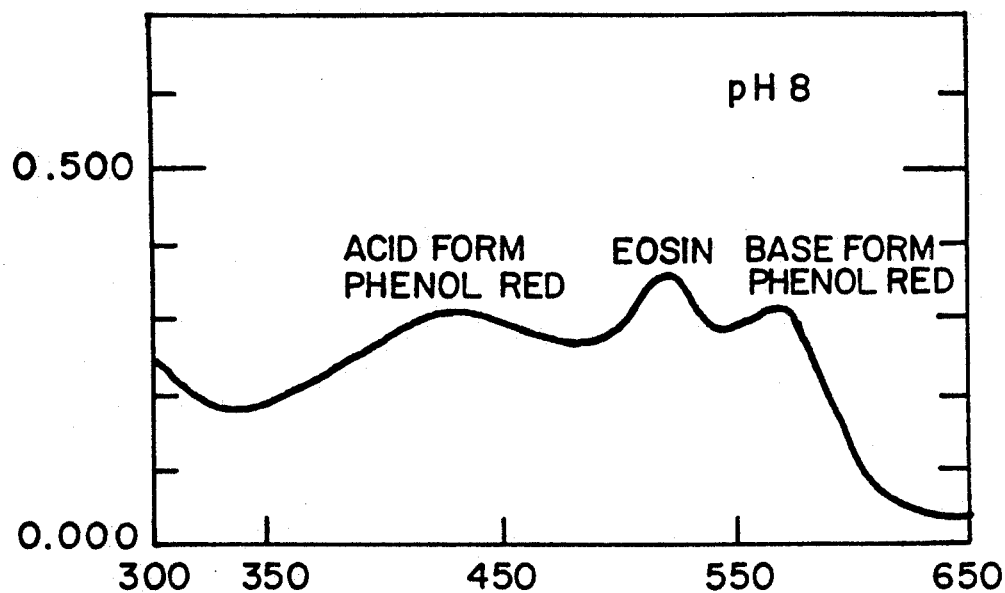
Figure 3D:
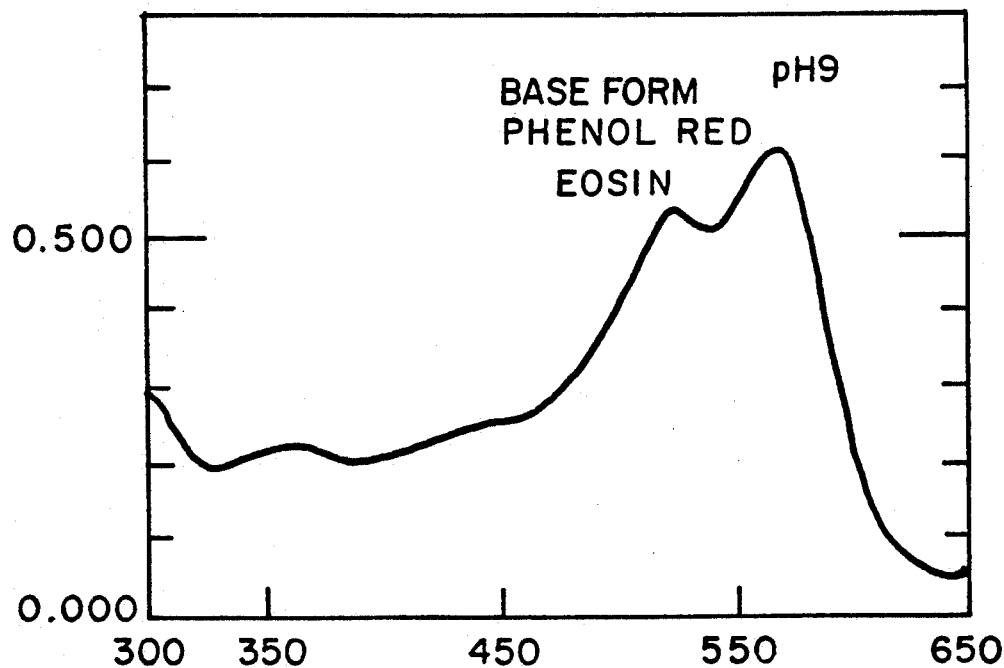

A conventional, standard arrangement for measuring fluorescence is intended to be used when practicing the methods comprising the present invention. Such an arrangement is illustrated in FIG. 2. As may be seen therein, a high-intensity light beam passes through a monochromater for the selection of an excitation wavelength, a light wavelength efficiently absorbed by the fluorophore. The exciting light beam then passes through a cell containing the fluid sample. To avoid detecting the incident beam, use is made of the fact that fluorescence is emitted in all directions so that observation of the emitted fluorescent light may be made at right angles to the incident beam. The emitted fluorescence then passes through a second monochromater for wavelength analysis and finally falls on a photosensitive detector, usually a photomultiplier tube or photodiode. It is expected that such instrumentation will have scanning systems and chart recorders that automatically vary the wavelength introduced as the exciting light and plot the intensity of the fluorescent light emitted as a function of wavelength of the emitted light. However, a simpler system employing filters for selecting incident and emitted light would suffice for many of the analytical applications.

Within the conventional instrumentation illustrated by FIG. 2, it is especially desirable that the means for introducing exciting light and the means for detecting the fluorescent light emitted by the reaction admixtures in the assay take the form of optical fiber strands. Such optical fibers can have terminal ends comprising glass surfaces or glass beads which have been chemically treated. The preparation and use of fiber optic strands has been described in: Milanovich et al., "Novel Optical Fiber Techniques For Medical Application," in *Proceedings Of The SPIE 28th Annual International Technical Symposium On Optics And Electrooptics*, Volume 494, 1985. The text of this publication is expressly incorporated by reference herein.

EMPIRICAL DATA

To demonstrate the value of the fluorophore-absorber conjugate composition as an effective reagent in detection methods generally, the following experiment is provided. It will be expressly understood, however, that while the described experiment is directed to detecting changes in pH, a variety of other fluorophore-absorber conjugates can be prepared for detection of many different analytes of interest; under no circumstances is the present invention said to be limited to any one application or the detection of only one analyte of interest.

All materials and instruments used in this work have been described in previously published papers [Jordan et al., *Anal. Chem.* 59:437 (1987); Yuan and Walt, *Anal. Chem.* 59:2391 (1987)]; therefore, only brief descriptions are presented here.

Materials

Eosin-5-isothiocyanate was purchased from Molecular Probes (Eugene, Oreg.). Dialysis membrane was from Spectrapor (Los Angeles, Calif.). All other chemicals were obtained from Aldrich Chemical Company. All purchased reagents were used without further purification, except for tetrahydrofuran (THF), which was freshly distilled just prior to use.

Glass-on-glass fibers (200/250 nm) were used. Glass capillary tubes were slipped over the fiber tips for protection.

Instruments

UV spectra were obtained with an IBM spectrophotometer. An argon-ion laser, Spectra-Physics Model 162A-04 (Mountain View, Calif.) provided the excitation radiation (488 nm). The intensity of the fluorescence was measured in photon counts and was selected as emission wavelengths with a Spex monochromater.

Preparation Of Polymer

An aqueous solution of acrylamide was prepared according to the procedure of Updike and Hicks [*Anal. Chem.* 38:726 (1966)]. The allyl eosin-5-thio urea was prepared immediately prior to use by mixing freshly distilled THF (1.0 ml) with eosin 5-isothiocyanate and adding allylamine after which the mixture was allowed to stand in the dark at room temperature for an hour.

Polymerization was performed by mixing the acrylamide solution and phenol red, which was deoxygenated with nitrogen. To the reaction, was added with stirring the THF solution of allyl eosin-5-thio urea, ammonium persulfate, and TEMED (N,N,N',N'-tetramethylethylenediamine). The mixture was allowed to stand at room temperature in a nitrogen atmosphere for an hour. Small-scale water soluble polymers were purified by bag dialysis (molecular weight cut-off $2 \times 10^3$ and $6 \times 10^3$) against pure water for 3 days.

Measurements

Buffer solutions were prepared in the manner of McIlvaine, and the pH values were verified by measurement prior to use. All pH response values were determined in replicate. All intensity measurements were observed at 545 nm, the emission maximum at room temperature.

Experimental Procedure And Results

Figure 4:
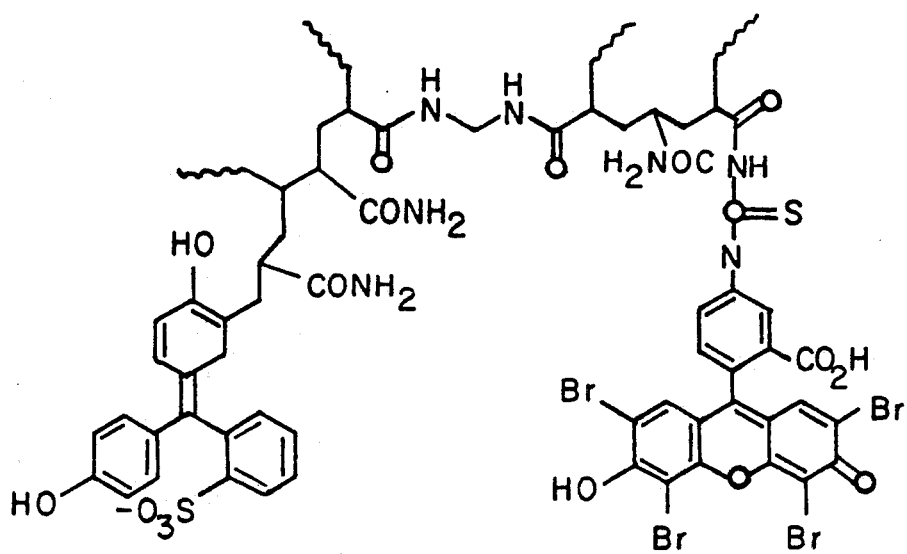
FIG. 4 is a structural representation of a fluorophore joined to an absorber as a conjugate composition suitable for use in intramolecular energy transfer.

Eosin-5-isothiocyanate was readily derivatized with an alkene function by reaction with allylamine. In addition, phenol red may be incorporated directly into acrylamide polymers without derivatization [Peterson et al., *Anal. Chem.* 52:864 (1980)]. It is believed that the polymerization reaction of phenol red with acrylamide succeeds because it possesses a quinone-like character and these experiments have confirmed this belief. After polymerization the reaction mixture was dialyzed with a 10,000 molecular weight cut-off membrane (Spectra Por). The UV spectrum for the resulting polymer solution provided by FIG. 3 shows strong absorption bands for both phenol red and eosin dyes indicating covalent incorporation of both dye moieties into the polymer chain. FIG. 4 symbolically illustrates the chemical structure of the two dyes—the fluorophore and the absorber—in the polymer. The ratio of the phenol red moieties to eosin moieties is not presently known because their relative rates of incorporation into the acrylamide chain has not been investigated; however, it is assumed that the distribution of both dyes in the polymer structure will be random.

Figure 5:
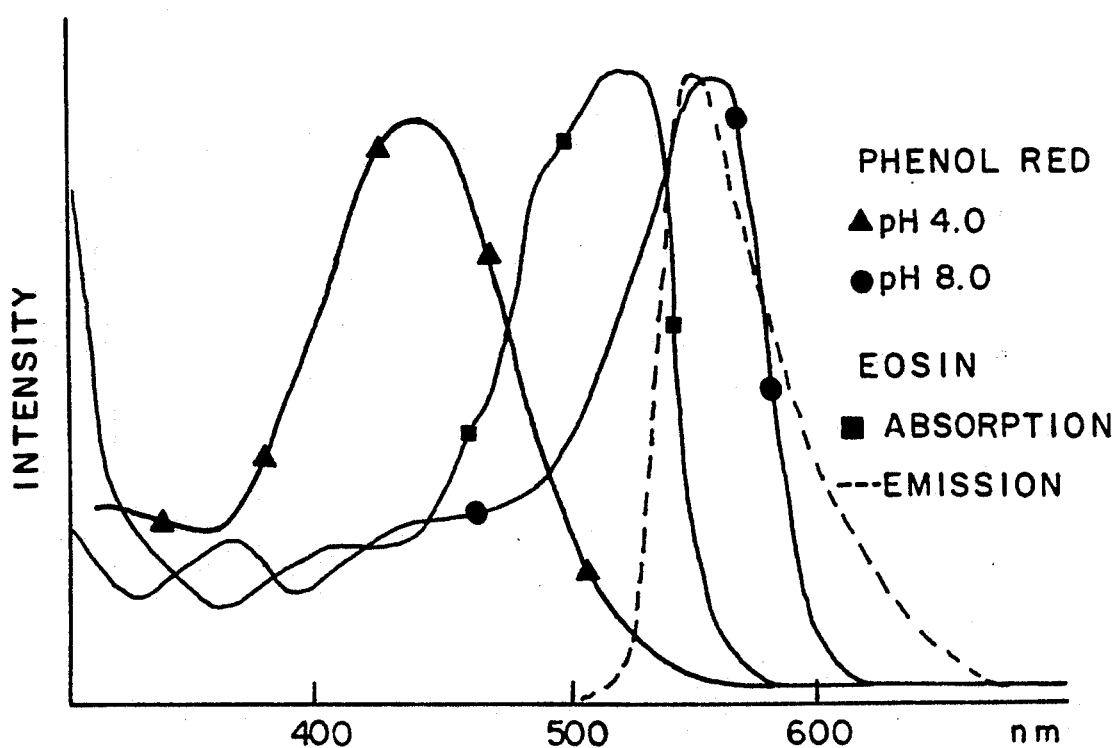
FIG. 5 is a graph illustrating the change in light absorption and light emission using phenol red and eosin with a change in pH from 4.0 to 8.0.

Table 1 shows the fluorescence intensities data of both the polymer and the two dyes mixture in buffers of pH 6 and pH 10 as a function of concentration. As is shown by FIG. 5., the absorption of the basic form of phenol red rises with increased pH and overlaps the emission spectrum of eosin. Consequently, non-radiative energy transfer increases as the pH is raised from 6 to 10.

TABLE 1

| RELATIVE CONCENTRATION (Ml) | RELATIVE SIGNAL RATIO (pH 10/pH6) (± relative standard deviation) | | | | | |
|---|---|---|---|---|---|---|
| | SAMPLE 1 | | SAMPLE 2 | | SAMPLE 3 | |
| | POLYMER | MIXTURE | POLYMER | MIXTURE | POLYMER | MIXTURE |
| 10 | 0.851 ± 0.047 | 0.985 ± 0.021 | 0.822 ± 0.024 | 0.945 ± 0.020 | 0.812 ± 0.059 | 0.973 ± 0.016 |
| 30 | 0.817 ± 0.019 | 0.940 ± 0.027 | 0.789 ± 0.033 | 0.937 ± 0.033 | 0.806 ± 0.048 | 0.959 ± 0.029 |
| 50 | 0.799 ± 0.012 | 0.895 ± 0.024 | 0.779 ± 0.032 | 0.892 ± 0.010 | 0.785 ± 0.045 | 0.955 ± 0.023 |
| 70 | 0.780 ± 0.034 | 0.867 ± 0.041 | 0.742 ± 0.027 | 0.863 ± 0.005 | 0.771 ± 0.045 | 0.939 ± 0.012 |
| 100 | 0.757 ± 0.034 | 0.848 ± 0.035 | 0.718 ± 0.018 | 0.877 ± 0.005 | 0.764 ± 0.031 | 0.913 ± 0.013 |
| 150 | 0.751 ± 0.013 | 0.782 ± 0.027 | 0.711 ± 0.017 | 0.795 ± 0.011 | 0.749 ± 0.040 | 0.890 ± 0.015 |
| 200 | 0.728 ± 0.013 | 0.77 ± 0.022 | 0.689 ± 0.021 | 0.753 ± 0.005 | 0.738 ± 0.046 | 0.841 ± 0.017 |

*The concentration for stock solution is about $5 \times 10^{-5}$ M.
**The concentration ratios for two dyes (eosin:phenol red) in the polymerizations: Sample 1 = 1:2.86 (mg); Sample 2 = 1:7 (mg); and Sample 3 = 1:2.25 (mg).

This increase is evident in the lower fluorescence intensity ratio from pH 10 to pH 6 at all concentrations of polymer. As a control, a two dye mixture was prepared in which the concentrations of donor and acceptor molecules were the same as in the polymer system as determined by the similarity in absorbance in the visible spectrum. As Table 1 demonstrates, there is only small fluorescence quenching from pH 6 to pH 10 except at high concentration in these preparations. The decrease in fluorescence intensity at pH 10 at high concentration is due primarily to inner filter effects. In the polymer solution, the ratio of the fluorescence intensity at pH 6 to pH 10 is almost constant while the ratio in the two dye mixture clearly increases with increased concentration. The local chromophores concentration on the polymer chain is constant and thus there is a fixed distance R between the two chromophores resulting in a concentration independent pH sensitivity. This spatial distance R has been estimated to be less than 100 Angstroms in all instances.

It is interesting to note that although the concentration of the two dyes is the same both in the polymer solution and in the mixture, the absolute fluorescence intensity signal in the mixture is larger than that in the polymer solution. The smaller fluorescence signal in the polymer is probably the result of a partial Dexter energy transfer and also an efficient Forster singlet energy transfer due to the small distance between two dyes.

Conclusions

The technique used in this series of experiments provides a method for determining the fluorescence quenching at very low absorber concentration via energy transfer in an intramolecular system. Under the described synthesis conditions, the distances of two dye moieties on the polymer chain are difficult to control because of the random polymerization. For this reason, a bichromophoric system composed of two dye moieties connected by a linker molecule is more desirable. This format will provide more definitive and controlled intramolecular energy transfer. It will be appreciated, however, that the efficient energy transfer in either of these systems will be useful in preparing a variety of new reversible fiber optic chemical sensors and analytical reagents.

ALTERNATIVE EMBODIMENTS

It will be appreciated that a wide range of different analyte-insensitive fluorophores can be combined with analyte-sensitive absorber molecules to form a conjugate composition such that the spatial distance between the two moieties is maintained at less than 100 Angstroms. A preferred listing of fluorophores and absorbers useful in diverse applications is provided by Table 2 below.

TABLE 2

| FLUOROPHORE | EXCITATION WAVELENGTH(S) (nm) | FLUORESCENCE EMISSION(S) (λmax) | ABSORBER | APPLICATION |
|---|---|---|---|---|
| Eosin | 520–530 | 530–580 nm (550 nm) | iron-salicylate complex | clinical salicylate analysis (Sigma Test No. 535) |
| TRITC-amine | 555 | 570–610 nm (590 nm) | chromophoric product of urea and diacetyl monoxime | clinical BUN analysis (Sigma Test No. 535) |
| Eosin | 520–530 | 530–580 nm | amaranth | measurement of amaranth released from complex with thorium and borate for sulfate analysis |
| TRITC-amine (or Eosin) | 555 | 570–610 nm | indamine dye | analysis of oxalate (Sigma Test No. 590) |
| Quinine | — | 530 nm | INT formazan dye | glucose analysis (Sigma Test No. 115) |
| Eosin | 520–530 | 550 nm | Hopkins-Cole dye | globulin analysis, total (Sigma Test No. 560) |
| Fluorescein W | 490–496 | 530 nm | calmagite-Mg complex | magnesium analysis (Sigma Test No. 595) |
| Eosin | 520–530 | 530–580 nm | peptide complex with cuprice ion | total protein analysis (Sigma Test No. 540) |
| TRITC-amine | 555 | 590 nm | molybdate complex | inorganic phosphate (Signa Test No. 670) |
| Eosin | 520–530 | 560 nm | Azin-bis-indandion $Cu^{+2}$ complex | cupric copper |
| Acridine yellow | 464 | 500 nm | quinone-imine dye | cholesterol, HDL (Sigma Test No. 351) |
| Eosin (or TRITC-amine) | 520–530 | | calcium-cresol-phthalein complex | calcium analysis (Sigma Test No. 586) |
| Lissamine | — | | $Fe(SCN)^{+2}$ | chloride ion analysis (Sigma Test No. 460) |
| Flavine FS | 416 | | | |
| Erthroscein | 504 | 560 nm | azobilirubin | Bilirubin analysis (Sigma Test No. 550) |
| Cyanosine B | 518 | | triose hydrazones | aldolase analysis (Sigma Test No. 750) |

The present invention is not limited in form nor restricted in scope except by the claims appended hereto.

What I claim is:

1. A method for detecting an analyte of interest in a fluid sample, said method comprising the steps of:
    admixing the fluid sample containing the analyte of interest with a fluid containing a preformed, fluorophore-absorber linked conjugate composition whose spectral characteristics are affected by contact with the analyte of interest to form a fluid reaction mixture, said preformed, fluorophore-absorber linked conjugate composition comprising
    (a) at least one fluorophore which is non-reactive with the analyte of interest, said fluorophore having characteristic and definable light absorption and light emission spectra, and which absorbs exciting light energy of a first wavelength, which transfers non-radiatively at least a portion of said exciting energy to an absorber, and which emit another portion of said exciting energy as emitted light of a second wavelength, (b) at least one absorber which is reactive with the analyte of interest and whose spectral characteristics are modulated by reactive contact with the analyte of interest, said absorber having a light absorption spectrum which overlaps in some degree with the definable light emission spectrum characteristic of said analyte non-reactive fluorophore, and which absorbs energy transferred non-radiatively by said analyte non-reactive fluorophore, and which is held at a spatial distance of not more than 100 Angstroms from said analyte non-reactive fluorophore, and (c) chemical linking agent means for holding said analyte reactive absorber at said spatial distance from said analyte non-reactive fluorophore within said conjugate composition;

introducing light energy of the first wavelength to said reaction mixture whereby said analyte non-reactive fluorophore of said conjugate composition absorbs said exciting light energy and emits an intensity of light of the second wavelength and wherein at least a portion of said exciting energy is non-radiatively transferred to and absorbed by said analyte reactive absorber of said conjugate composition; and determining the intensity of said emitted light of the second wavelength from said reaction mixture, said intensity of emitted light being a measure of the analyte of interest in the sample.

2. A method for detecting an analyte of interest in a fluid sample, said method comprising the steps of:

admixing the fluid sample containing the analyte of interest with a fluid containing a preformed, fluorophore-absorber linked conjugate composition whose spectral characteristics are affected by contact with the analyte of interest to form a fluid reaction mixture, said preformed, fluorophore-absorber linked conjugate composition comprising (a) at least one fluorophore which is non-reactive with the analyte of interest, said fluorophore having characteristic and definable light absorption and light emission spectra, and which absorbs exciting light energy of a first wavelength, and which transfers non-radiatively substantially all of said exciting energy to an absorber such that there then is an absence of emitted light energy of a second wavelength, (b) at least one absorber which is reactive with the analyte of interest and whose spectral characteristics are modulated by reactive contact with the analyte of interest, said absorber having la light absorption spectrum which overlaps in some degree with the definable light emission spectrum characteristic of said analyte non-reactive fluorophore, and which absorbs energy transferred non-radiatively by said analyte non-reactive fluorophore, and which is held at a spatial distance of not more than 100 Angstroms from said analyte non-reactive fluorophore, and (c) chemical linking agent means for holding said analyte reactive absorber at said spatial distance from said analyte non-reactive fluorophore within said conjugate composition;

introducing light energy of the first wavelength to said reaction mixture whereby said analyte non-reactive fluorophore of said conjugate composition absorbs said exciting light energy without subsequently emitting light energy of a second wavelength and wherein substantially all of said exciting energy is non-radiatively transferred to and absorbed by said analyte reactive absorber of said conjugate composition; and determining the absence of emitted light energy of the second wavelength from said reaction mixture, said absence of emitted light energy being a measure of the analyte of interest in the sample.

3. The detection method as recited in claim 1 or 2 wherein said introduction of light energy is achieved using an optical fiber.

4. The detection method as recited in claim 1 or 2 wherein said determining of emitted light is made using a fiber optic sensor.

* * * * *